United States Patent [19] [11] 4,334,529
Wirth [45] Jun. 15, 1982

[54] WIRTH'S STERILE, DISPOSABLE SURGICAL DRAPE

[75] Inventor: Carl R. Wirth, Slingerlands, N.Y.

[73] Assignees: Caroline G. Wirth, Slingerlands; Roberta H. Wessendorf, Guilderland, both of N.Y.; a part interest

[21] Appl. No.: 253,944

[22] Filed: Apr. 14, 1981

[51] Int. Cl.³ ............................................. A61F 13/00
[52] U.S. Cl. ............................................. 128/132 D
[58] Field of Search ........................ 128/132 R, 132 D

[56] References Cited

U.S. PATENT DOCUMENTS

| Re. 26,759 | 1/1970 | Melges | 128/132 D |
|---|---|---|---|
| Re. 27,710 | 7/1963 | Melges | 128/132 D |
| 1,491,011 | 4/1924 | Hodgin | 128/132 D |
| 1,724,443 | 8/1929 | Wheeler | 128/132 D |
| 2,591,783 | 4/1952 | Craddock | 128/132 D |
| 2,593,121 | 4/1952 | Djorup | 128/132 D |
| 3,030,957 | 4/1962 | Melges | 128/132 D |
| 3,060,932 | 10/1962 | Pereny et al. | 128/132 D |
| 3,068,863 | 12/1962 | Bowman | 128/132 D |
| 3,154,789 | 11/1964 | Lewis, Jr. | 128/132 D |
| 3,182,656 | 5/1965 | Pyne | 128/132 D |
| 3,236,370 | 2/1966 | Pereney et al. | 128/132 D |
| 3,251,360 | 5/1966 | Melges et al. | 128/132 D |
| 3,260,260 | 7/1966 | Questel | 128/132 D |
| 3,263,680 | 8/1966 | Morgan | 128/132 D |
| 3,300,786 | 1/1967 | Rosenvold et al. | 128/132 D |
| 3,397,692 | 8/1968 | Creager, Jr. et al. | 128/132 D |
| 3,410,266 | 11/1968 | Krzewinski et al. | 128/132 D |
| 3,416,520 | 12/1968 | Creager, Jr. | 128/132 D |
| 3,424,153 | 1/1969 | Lewis, Jr. | 128/132 D |
| 3,435,821 | 4/1969 | Bennett | 128/132 D |
| 3,482,567 | 12/1969 | Franklin | 128/132 D |
| 3,484,330 | 12/1969 | Sokoloski | 128/132 D |
| 3,503,391 | 3/1970 | Melges | 128/132 D |
| 3,537,446 | 4/1970 | Rowland, Jr. et al. | 128/132 D |
| 3,565,067 | 2/1971 | Bayer et al. | 128/132 D |
| 3,569,439 | 2/1971 | Bayer | 128/132 D |
| 3,569,440 | 2/1971 | Bayer | 128/132 D |
| 3,589,365 | 6/1971 | Sejman | 128/132 D |
| 3,669,106 | 6/1972 | Schrading et al. | 128/132 D |
| 3,721,234 | 3/1973 | Hadtke et al. | 128/132 D |
| 3,776,217 | 12/1973 | van Galen et al. | 128/1 B |
| 3,791,382 | 2/1974 | Collins | 128/132 D |
| 3,799,161 | 3/1974 | Collins | 128/132 D |
| 3,856,006 | 12/1974 | Krzewinski | 128/132 D |
| 3,871,369 | 3/1975 | Krzewinski | 128/132 D |
| 3,881,474 | 5/1975 | Krzewinski | 128/132 D |
| 3,882,859 | 5/1975 | Ericson | 128/132 D |
| 3,889,667 | 6/1975 | Collins | 128/132 D |
| 3,910,268 | 10/1975 | Miller | 128/132 D |
| 3,927,667 | 12/1975 | Criddle et al. | 128/132 D |
| 3,942,523 | 3/1976 | Rudtke | 128/132 D |
| 3,956,048 | 5/1976 | Nordgren | 128/132 D |
| 4,027,665 | 6/1977 | Scrivens | 128/132 D |
| 4,033,341 | 7/1977 | Scrivens | 128/132 D |
| 4,089,331 | 5/1978 | Hartigan et al. | 128/132 D |
| 4,134,398 | 1/1979 | Scrivens | 128/132 D |

Primary Examiner—Kyle L. Howell
Assistant Examiner—C. W. Shedd
Attorney, Agent, or Firm—Walter F. Wessendorf, Jr.

[57] ABSTRACT

Discloses a sterile, disposable surgical drape having top and bottom layers sandwiching therebetween a blank of elastic material having equally-spaced holes. The top and bottom layers have aligned square openings exposing thereby said elastic material and holes. Covering tabs having sealing tabs seal the openings in the top layer and lift tabs to facilitate manipulative removal of the covering tabs.

The drape is specifically designed and constructed so that tubing, wiring, cables, and the like that are operatively connected to non-sterile equipment may be sterilized and neatly arranged and carried by the spaced holes of the drape.

1 Claim, 9 Drawing Figures

WIRTH'S STERILE, DISPOSABLE SURGICAL DRAPE

BACKGROUND OF THE INVENTION

1. Technical Field

This invention relates to sterile, disposable surgical drapes for covering a surgical patient in the operating room on the operating table, and for providing and maintaining a sterile field in which a surgeon can operate or perform other diagnostic procedures.

2. Background Art

The prior art, U.S. Pat. No. 1,491,011 discloses a living cavity shield; U.S. Pat. No. 1,724,443 discloses an obstetrical sheet; U.S. Pat. No. 2,591,783 discloses a protecting shield; U.S. Pat. No. 2,593,121 discloses a medical examination drape; U.S. Pat. No. 3,030,957 discloses a disposable obstetrical and/or surgical cover means; U.S. Pat. No. 3,060,932 discloses a sterile surgical drape and method; U.S. Pat. No. 3,068,863 discloses protective devices; U.S. Pat. No. 3,154,789 discloses a disposable examination garment; U.S. Pat. No. 3,182,656 discloses a surgical sheet; U.S. Pat. No. 3,236,370 discloses a sterile surgical drape; U.S. Pat. No. 3,251,360 discloses a gynecology or lithotomy drape; U.S. Pat. No. 3,260,260 discloses a surgical drape or laminate; U.S. Pat. No. 3,263,680 discloses a surgical or vaginal drape; U.S. Pat. No. 3,300,786 discloses an eye shield blank and method of assembling same; U.S. Pat. No. 3,397,692 discloses a protector for incised wounds; U.S. Pat. No. 3,410,266 discloses a surgical apparel; U.S. Pat. No. 3,416,520 discloses a surgical drape; U.S. Pat. No. 3,424,153 discloses a disposable surgical legging; U.S. Pat. No. 3,435,821 discloses a surgical drape; U.S. Pat. No. 3,484,330 discloses a disposable fabric; U.S. Pat. No. Re. 26,759 discloses a gynecology or lithotomy drape; U.S. Pat. No. 3,503,391 discloses a non-woven surgical shield or cover member; U.S. Pat. No. 3,537,446 discloses a fenestrated surgical drape; U.S. Pat. No. 3,561,439 discloses a laparotomy sheet with plastic center strip having absorbent layer; U.S. Pat. No. 3,561,440 discloses self-adhering tabs for surgical drapes and garments; U.S. Pat. No. 3,565,067 discloses a laparotomy sheet with plastic reinforcement; U.S. Pat. No. 3,589,365 discloses an underbuttocks drape; U.S. Pat. No. 3,669,106 discloses a surgical drape with adhesive attachment means; U.S. Pat. No. 3,721,234 discloses a disposable surgical cover sheet; U.S. Pat. No. Re. 27,710 discloses a non-woven surgical shield or cover member; U.S. Pat. No. 3,791,382 discloses waterproof body coverings with fluid receiving pockets; U.S. Pat. No. 3,799,161 discloses a multiple purpose drape; U.S. Pat. No. 3,856,006 discloses surgical drapes with improved arm coverage; U.S. Pat. No. 3,881,474 discloses a reinforced surgical drape; U.S. Pat. No. 3,882,859 discloses an elastic fenestrated drape; U.S. Pat. No. 3,889,667 discloses a surgical drape; U.S. Pat. No. 3,910,268 discloses a surgical drape; U.S. Pat. No. 3,927,667 discloses a diffuser drape; U.S. Pat. No. 3,942,523 discloses a reinforced double-fenestrated surgical drape; U.S. Pat. No. 3,956,048 discloses a method for the manufacturing of a disposable operation textile; U.S. Pat. No. 4,033,341 discloses a surgical drape having improved retaining means; U.S. Pat. No. 4,089,331 discloses a surgical drape with fenestration liner; U.S. Pat. No. 4,134,398 discloses a surgical drape having improved retaining means; U.S. Pat. No. 3,871,369 discloses a self-adhesive surgical apparel and method; and U.S. Pat. No. 4,027,665 discloses a cardiovascular drape.

A sterile operating field can be bacterially contaminated by bringing non-sterile equipment such as an intravenous bag, TV camera, IV pole, auxiliary equipment table, light source, battery pack, up to or against a sterile surgical drape covering the patient. Tubing, wiring, cables, and the like, associated with such equipment, and lying upon the operating table, provide a path along which bacteria may migrate to bacterially contaminate such sterile operating field. Anytime tubing, wiring, cables, and the like, or associated equipment, is disposed, or is allowed to be disposed, below the plane of the operating table, such condition of non-sterility or bacterial contamination is, or is deemed to have been, introduced into such sterile operating field and hence the surgical procedure or operation being performed. Such tubing, wiring, cables, and the like, must be restricted in their functional lengths to remain on the plane of the operating table lest their otherwise excessive lengths will cause same to be disposed below the operating-table plane and cause such bacterial contamination of the sterile operating field. Such tubing, wiring, cables, and the like, possess a degree of inflexibility such that their movement or disposition under prior-art conditions will effect and cause lifting-away or movement of the sterile surgical drape away from the patient when such tubing, wiring, cables, and the like, are trained around the edges of such surgical drape thereby permitting bacterial contamination of such sterile operating field.

Accordingly, the object of the invention is to contribute to the solution of the discussed problems of the prior art by providing a sterile, disposable surgical drape specifically designed and constructed so that tubing, wiring, cables, and the like, that are to be operatively connected to such non-sterile equipment, can be sterilized and neatly arranged and carried by such surgical drape while maintaining such sterile operating field relative to such patient, whether such non-sterile equipment is disposed under such drape or away from such sterile operating field. Not only can those portions of such tubing, wiring, cables, and the like, which will be exposed in such sterile operating field, can be restricted to workable and practicable lengths to perform their intended functions, but also such restrictions in their lengths will prevent same from being disposed below the operating-table plane.

SUMMARY OF THE INVENTION

In accordance with the invention, there is provided a sterile, disposable surgical drape of suitable material having a top layer and a bottom layer sandwiching therebetween a rectangular blank of elastic material having very small holes therethrough. Such very small holes are covered and sealed by removable, sterile, folded-back tabs. The sterile, surgical drape of this invention permits such equipment to be utilized in connection with the operation or surgical procedure, to be disposed either or both under such sterile drape and away from such sterile operating field to maintain the sterile operating field relative to the patient. Those portions of such tubing, wiring, cables, and the like—to be used with such equipment and to be exposed in such sterile operating field—can be sterilized and disposed in retentive relationship with and through such very small holes after their corresponding sterile covering tabs have been removed. Furthermore, such exposed tubing, wiring, cables, and the like, can be restricted to workable and practicable lengths both to neatly and conveniently facilitate their performing their intended functions, and to prevent or minimize the possibility of any such tubing, wiring, cables, and the like, being bacterially contaminated by disposition below the operating-table plane. The very small holes hold and retain very tightly such tubing, wiring, cables, and the like. Since none of the tubing, wiring, cables, and the like, is disposed or trained around the edges of the sterile drape, but disposed through such sterile drape, such sterile drape will not be lifted-away or moved-away from the patient to bacterially contaminate such sterile operating field.

BRIEF DESCRIPTION OF THE DRAWINGS

This object and other objects of the invention should be discerned and appreciated by reference to the drawings, wherein like reference numerals refer to similar parts throughout the several views, in which.

DESCRIPTION OF THE PREFERRED EMBODIMENT

Figure 1:
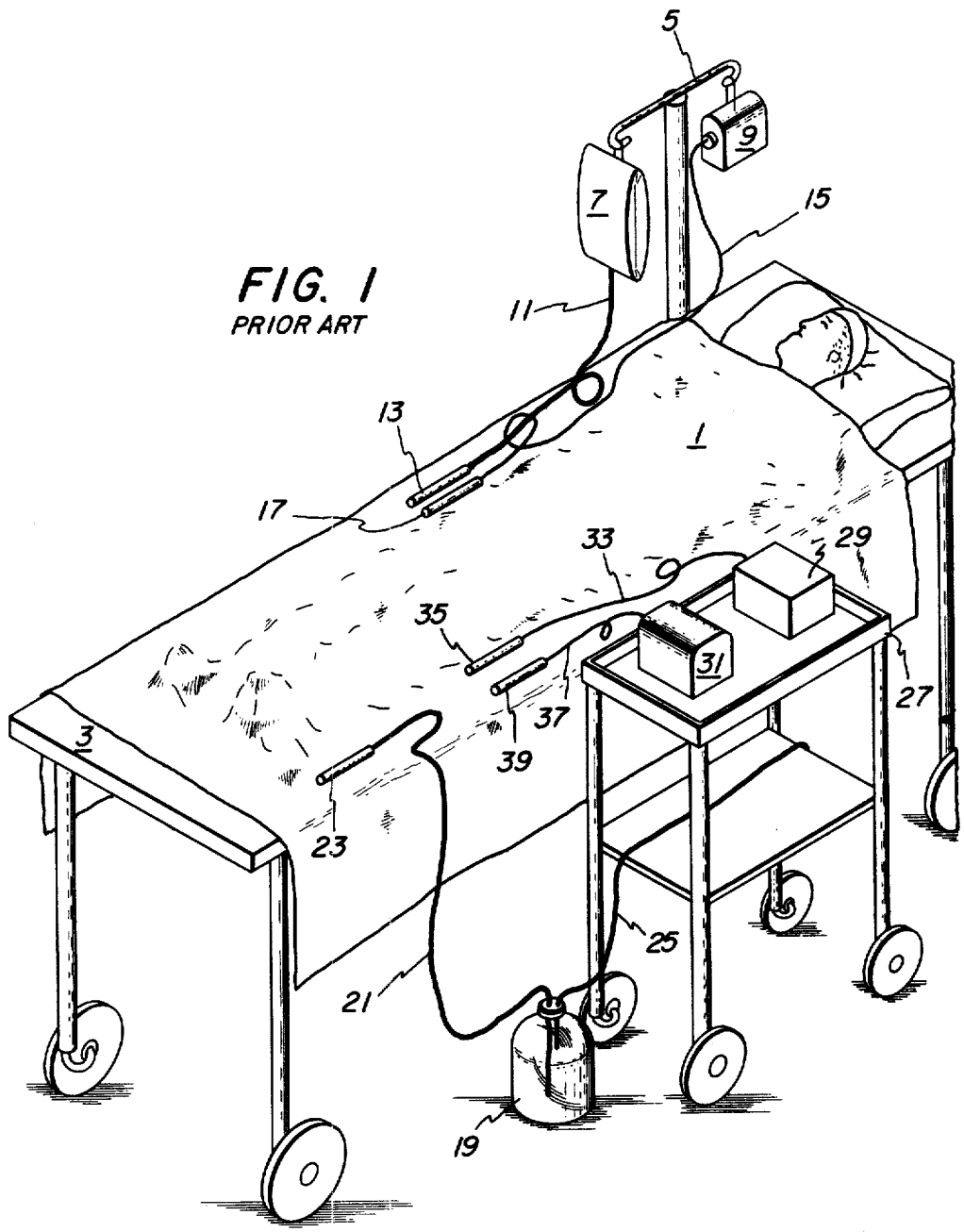
FIG. 1 is a view showing an example of prior-art use and employment of a surgical drape preparatory to performing an operation.

FIG. 1 of the drawings shows an example of prior-art use and employment of a surgical drape 1 preparatory to performing an operation on the patient lying on the operating table 3. An IV pole 5 mounts an intravenous bag 7 and TV camera 9. Tubing 11 from intravenous bag 7 lies upon drape 1 alongside the patient and has a coupling 13 at its end. Flexible cable 15 leads from TV camera 9, lies upon drape 1 alongside the patient and has a coupling 17 at its end. A suction bottle 19 is on the operating room floor. Tubing 21 from suction bottle 19, lies upon drape 1 along the other side of the patient and has a coupling 23 at its end; and tubing 25, leading from the suction bottle 19 to join wall suction, is partially shown. An auxiliary equipment table 27 next to the operating table 3 carries thereon a battery pack 29 and light source 31. Wiring 33 leads from battery pack 29, lies upon drape 1 and has a male jack 35 at its end. Fiber-optic cable 37 leads from light source 31, lies upon drape 1 and has a coupling 39 at its end.

From this description of FIG. 1 and the prior-art use and employment of the surgical drape 1 along with equipment and associated tubing, wiring and cables, it should be discerned and appreciated that problems of the prior art of bacterial contamination of the sterile operating field have been depicted and described. The IV pole 5, intravenous bag 7, TV camera 9, suction bottle 19, auxiliary equipment table 27, battery pack 29 and light source 31 are all nonsterile. Tubing 21 below the plane of the operating table 3 and tubing 25, by themselves, have, or are deemed to have, introduced bacterial contamination of the sterile operating field. Further, tubing 11, flexible cable 15, tubing 21, wiring 33 and fiber-optic cable 37 provide paths along which bacteria from such non-sterile equipment may migrate to bacterially contaminate the sterile operating field defined by the area generated by the sterile drape 1 covering the patient at and above the plane of the operating table 3.

Figure 2:
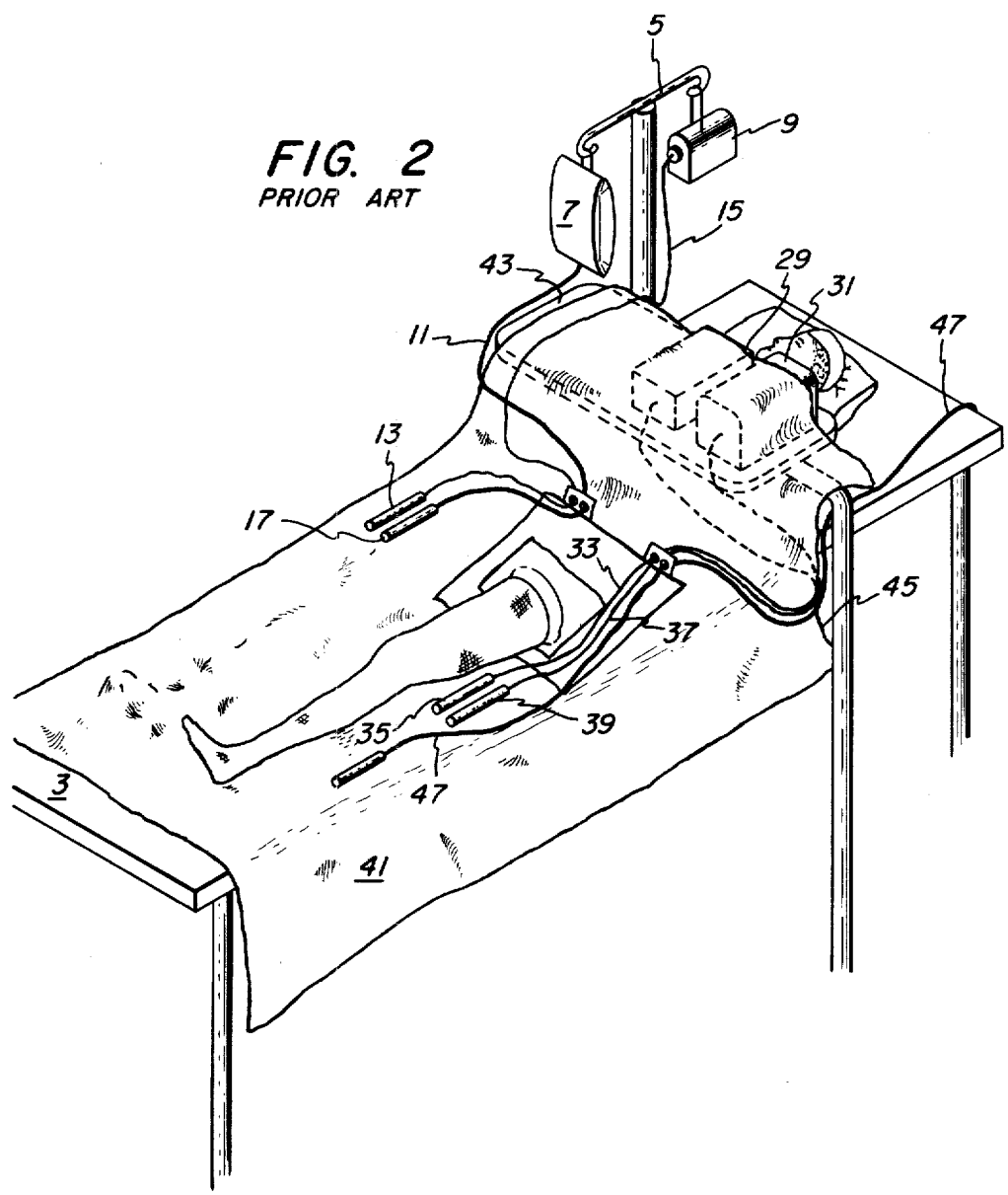
FIG. 2 is a view showing an example of prior-art use and employment of a surgical drape preparatory to arthroscopy.

FIG. 2 shows an example of prior-art use and employment of a sterile, surgical drape 41 preparatory to arthroscopy. The intravenous bag 7 and TV camera 9 mounted by IV pole 5 have respective tubing 11 and flexible cable 15 lying upon drape 41 alongside the patient. An auxiliary equipment stand 43 carries battery pack 29 and light source 31 whose respective wiring 33 and fiber-optic cable 37 lie upon drape 41 and are trained around an edge 45 of drape 41, as does suction tubing 47 lying upon drape 41, trained around such edge 45 of drape 41 and leading to wall suction (not shown), thereby lifting-away or moving-away such drape 41 from the patient and thereby permitting bacterial contamination of the sterile operating field defined by the area generated by the sterile drape 41 covering the patient at and above the plane of the operating table 3. Tubing 11, flexible cable 15, wiring 33, fiber-optic cable 37 and suction tubing 47, likewise, provide paths along which bacteria from non-sterile equipment may migrate to bacterially contaminate the sterile operating field.

Figure 3:
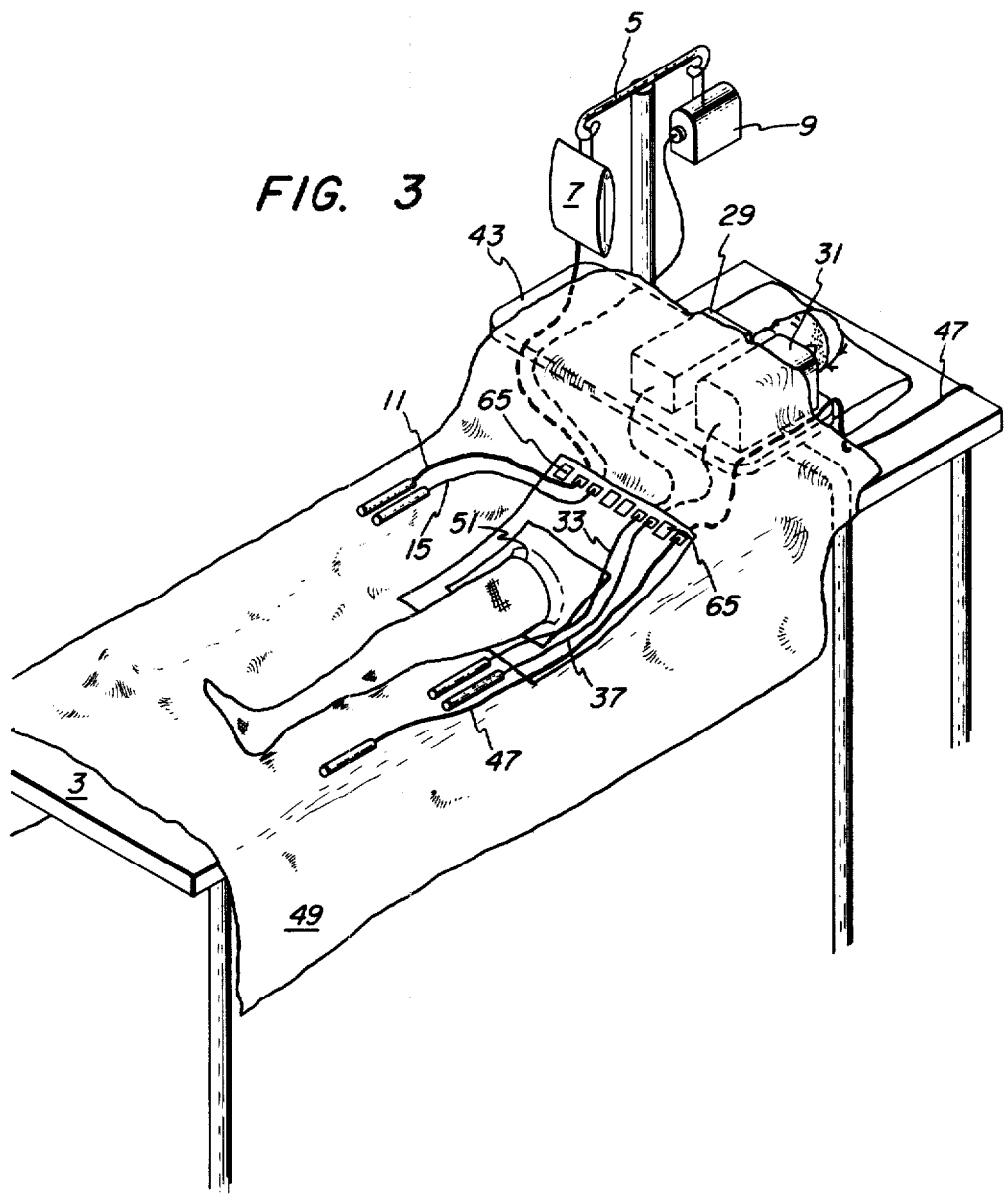
FIG. 3 is a view showing the use and employment of a sterile, disposable surgical drape of this invention, preparatory to arthroscopy and modified therefor.
Figure 4:
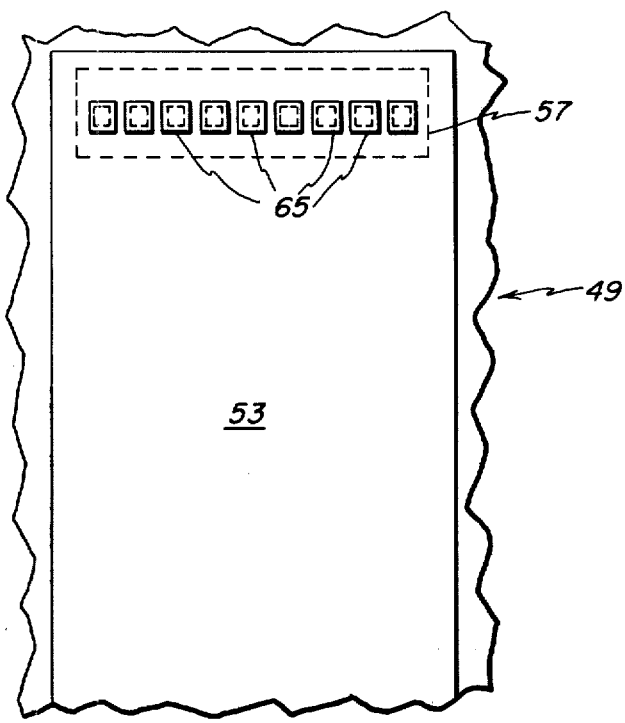
FIG. 4 is a top view of a portion of the sterile, surgical drape of this invention.
Figure 5:
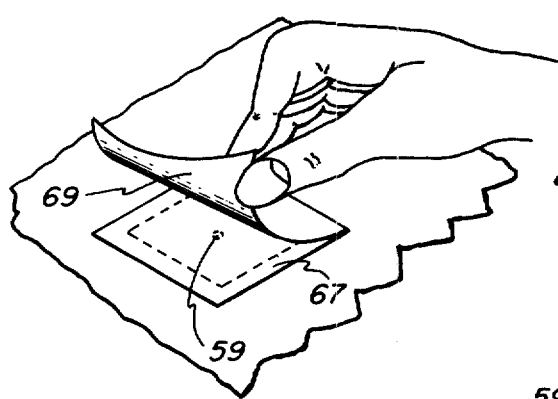
FIG. 5 is a view of a covering tab sealing one of the very small holes in the elastic material.
Figure 6:
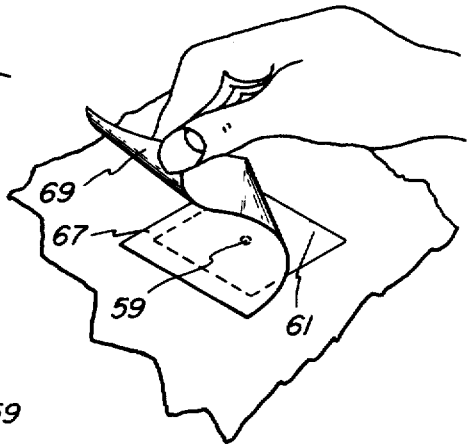
FIG. 6 is a view of such covering tab in FIG. 5 partially removed.
Figure 7:
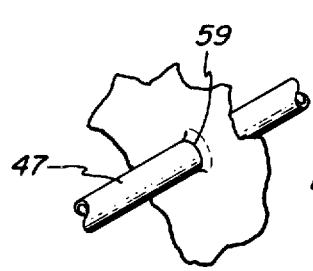
FIG. 7 is a view showing a very small hole in such elastic material tightly carrying tubing transversely disposed therethrough.
Figure 8:
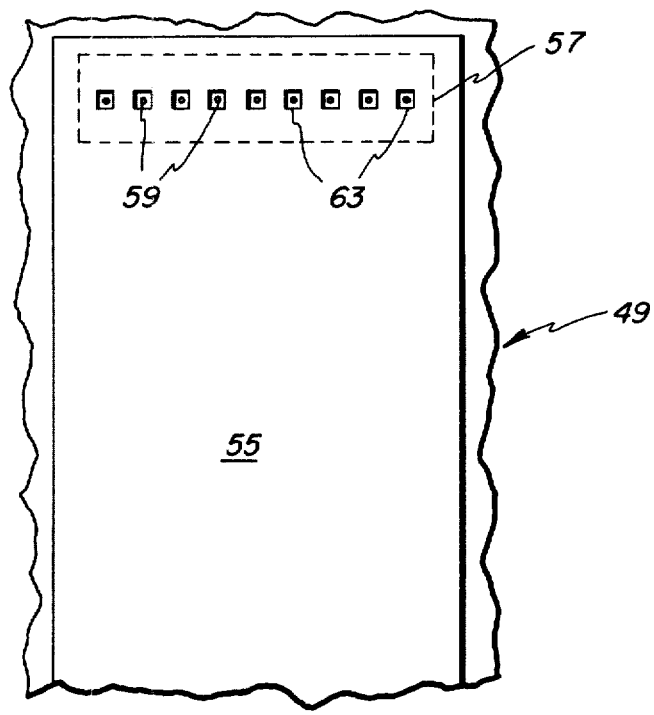
FIG. 8 is a bottom view of FIG. 4.
Figure 9:
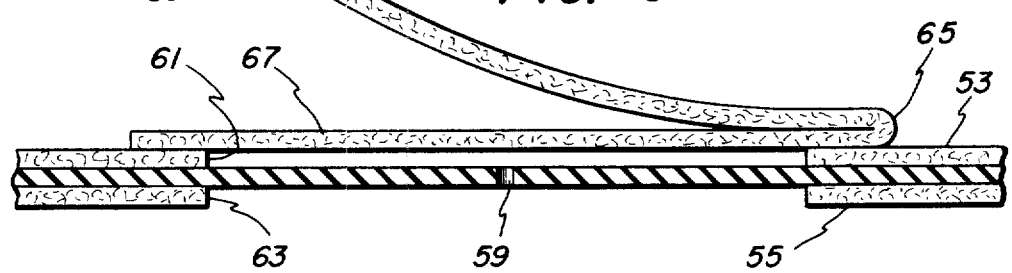
FIG. 9 is a view of a portion of the surgical drape of this invention with such elastic material sandwiched between the top and bottom layers, and with a covering tab sealing a very small hole in such elastic material.

FIG. 3 shows the use and employment of the sterile, disposable surgical drape 49 of this invention. Drape 49 is modified for arthroscopy by having a suitable hole 51 formed therethrough which tightly engages the covered leg projected through hole 51, and upon which the diagnostic or operative procedure is to be performed, to maintain the sterile operating field defined by the area generated by the sterile drape 49 covering the patient at or above the plane of the operating table 3.

With reference to FIGS. 4-9, the sterile, disposable surgical drape 49 of this invention has a top layer 53 and a bottom layer 55 sandwiching therebetween a rectangular blank 57 of suitable, elastic material having therealong a plurality of equally-spaced, very small holes 59 therethrough. Formed through the top and bottom layers 53 and 55 are aligned, square-shaped openings 61 and 63, respectively, which expose such elastic material of the rectangular blank 57 and the very small holes centered therewith. Each of the covering tabs 65 has a sealing tab 67 coated or otherwise formed with a suitable adhesive for adhesion of sealing tab 67 to the portion of the top layer 53 bordering on opening 61 to thereby seal top layer 53 and maintain the sterile condition of drape 49. Each covering tab 65 has a folded-back lift tab 69 that a human operator can engage between his thumb and index finger to pull away and remove the sealing tab sealing an opening in top layer 53.

With reference again to FIG. 3, the IV pole 5, intravenous bag 7 and TV camera 9 are non-sterile, but their respective tubing 11 and flexible cable 15 cannot bacterially contaminate the sterile operating field because those portions of such tubing 11 and flexible cable 15, to be exposed in such sterile operating field, were sterilized, then inserted tightly through conveniently located holes 59 of such elastic material and then operatively connected to their respective intravenous bag 7 and TV camera 9. The battery pack 29 and light source 31 are non-sterile, but their respective wiring 33 and fiber-optic cable 37 cannot bacterially contaminate the sterile operating field because those portions of such wiring 33 and cable 37, to be exposed in such sterile operating field were sterilized, then inserted through conveniently located holes 59 of such elastic material and then operatively connected to their respective battery pack 29 and light source 31. The same procedure was followed with respect to suction tubing 47. The covering tabs 65 remain over the openings 61 whose small holes 59 are not being used, thereby maintaining the sterile condition of drape 49 and the sterile operating field. The lengths of the tubing 11, cable 15, wiring 33, fiber-optic cable 37 and suction tubing 47 that are disposed upon and lie upon the drape 49 are restricted to the workable and practicable lengths to neatly and conveniently facilitate performance of their intended functions. The remaining portions of such tubing 11, cable 15, wiring 33, fiber-optic cable 37 and suction tubing 47 are disposed beneath the sterile drape 49 and away from the sterile operating field being maintained.

Having thusly described my invention, I claim:

1. A sterile, disposable surgical drape for covering a surgical patient on the operating table, and for providing and maintaining a sterile field in which a surgeon can operate or perform other diagnostic procedures requiring the use of tubing, wiring, cables, or the like, operatively connected to non-sterile equipment; said surgical drape comprising top and bottom layers, elastic material, very small holes, openings and covering tabs, said top and bottom layers sandwiching said elastic material therebetween, said very small holes being in said elastic material, said very small holes being substantially, equally-spaced thereon, said very small holes functioning to tightly hold and retain said tubing, cables, wiring and the like, said openings being in said top and bottom layers, said openings being in aligned relationship, said openings exposing said elastic material and said very small holes, said very small holes being substantially centered within said openings, said covering tabs having sealing tabs to seal said openings and maintain the sterile condition of said drape, said covering tabs having lift tabs engageable in manipulative relationship to pull away and remove said sealing tabs sealing said openings and to thereby expose said very small holes; and whereby said tubing, wiring, cables, and the like, may be sterilized, and neatly arranged and carried by said very small holes, whereby those portions of said tubing, wiring, cables, and the like, exposed in such sterile operating field, may be restricted to workable and practicable lengths to both perform their intended functions and to prevent same from being disposed below the operating-table plane and from thereby introducing the condition of non-sterility or bacterial contamination into such sterile operating field, and whereby said tubing, wiring, cables, and the like, being disposed through and carried by said very small holes, prevents same from lifting said sterile drape away from or moving said sterile drape away from such patient to bacterially contaminate such sterile operating field, and whereby such drape, so arranged and constructed, cooperatively functions to prevent bacterial contamination of such sterile operating field regardless of whether said non-sterile equipment is disposed or located under said drape or away from such sterile operating field.

* * * * *